United States Patent
Yoshida

(10) Patent No.: US 6,630,598 B2
(45) Date of Patent: Oct. 7, 2003

(54) PROCESS FOR PRODUCING N-ACYLNITROANILINE DERIVATIVE

(75) Inventor: Tomoyasu Yoshida, Ibaraki (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/903,489

(22) Filed: Jul. 12, 2001

(65) Prior Publication Data

US 2002/0016506 A1 Feb. 7, 2002

(30) Foreign Application Priority Data

Jul. 13, 2000 (JP) .................................. 2000-212693

(51) Int. Cl.⁷ .......................................... C07C 205/00
(52) U.S. Cl. .............................. 560/20; 560/21; 560/22; 560/23
(58) Field of Search ...................... 560/22, 20, 21, 560/23

(56) References Cited

FOREIGN PATENT DOCUMENTS

| EP | 0 745 600 A1 | 12/1996 |
| EP | 1 172 356 A | 1/2002 |
| WO | WO 90/12783 | 11/1990 |

OTHER PUBLICATIONS

Dalla Croce et al, Selective Monoalkylation of Amines, Journal of Chemical Research (S), 1988, pp. 346–347.*
Solomons, Organic Chemistry 1992, John Wiley & Sons, Inc. New York, pp. 241 and 774–778.*
Patent Abstracts of Japan, vol. 005, No. 152, (C073), Sep. 25, 1981.
H. Tye et al, "Design, synthesis and preliminary studies on a novel class of chiral receptor for the recognition of amino acid derivatives", J. Chem. Soc., Perkin Transactions 1, (1998), pp. 457–465.
Database Crossfire Beilstein, No. (XP002178675), 1998.
Database Crossfire Beilstein, No. (XP002178676), 1990.
T.A. Kelly et al., A Simple Method for the Protection of Aryl Amines as their t–Butylcarbamoyl (Boc) Derivatives, Tetrahedron Letters, vol. 35, No. 48, (1994), pp. 9003–9006 with Abstract.
Database Crossfire Beilstein, No. (XP002178677), 1957.
Database Crossfire Beilstein, No. (XP002178678), 1940.
Database Crossfire Beilstein, No. (XP002178679), 1942.
Database Crossfire Beilstein, No. (XP002178680), 1973.
Database Crossfire Beilstein, No. (XP002178681), 1985.

* cited by examiner

Primary Examiner—Samuel Barts
Assistant Examiner—Paul A. Zucker
(74) Attorney, Agent, or Firm—Sughrue Mion, PLLC

(57) ABSTRACT

A process of reacting a nitroaniline compound of formula (2):

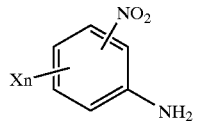

(2)

with an acid anhydride or acid halide is carried out in the presence of an alkali metal compound or an alkaline earth metal compound to produce an acylnitroaniline derivative. The process further includes the step of reacting the resulting product with a compound of formula (5);

$R^2$—Y to produce an N-acylnitroaniline derivative of formula (1):

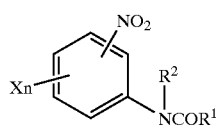

(1)

The N-acylnitroaniline derivative of formula (1) is a useful intermediate for the production of pharmaceuticals.

21 Claims, No Drawings

PROCESS FOR PRODUCING N-ACYLNITROANILINE DERIVATIVE

FIELD OF THE INVENTION

The present invention relates to a method for producing N-acylnitroaniline derivatives and, more specifically, an N-acylnitroaniline derivative of formula (4) as shown below, which is useful as an intermediate in the production of pharmaceutical or agricultural products.

DESCRIPTION OF RELATED ART

A method for producing an N-acylnitroaniline derivative of formula (4) is known which includes the steps of N-acylation of a nitroaniline compound with an acylating agent, such as di-tert-butyl dicarbonate, in the presence of a base, such as 4-N,N-dimethylaminopyridine or the like, and an N-alkylating reaction of the N-acylated product (Japanese Patent Laid-Open Hei 9-295970 (1997)).

However, the method described above has problems in that the yield is not always satisfactory, and a purification process by crystallization was required in the step of N-acylation since large amounts of impurities are present.

Hence, development of an industrially advantageous production method for producing N-acylnitroaniline derivatives of formulas (1) and (4) has been desired.

SUMMARY OF THE INVENTION

According to the present invention, N-acylation of nitroaniline compounds can be selectively conducted by using an alkali metal compound or an alkaline earth metal compound in an amount of about 1.6 moles or more per mol of a nitroaniline, and further derivatization thereafter can proceed smoothly to give a desired N-substituted N-acylnitroaniline derivative in a good yield.

Thus, the present invention provides a method for producing an N-acylnitroaniline derivative of formula (1);

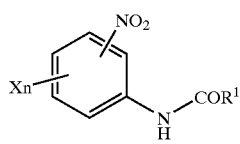

(1)

wherein X may be the same or different and each denotes a hydrogen atom; a halogen atom; an alkyl group; a haloalkyl group; an alkoxy group; a phenylalkyl group; a phenylalkoxyl group;

a phenyl group which may be optionally substituted with a halogen, a nitro group, an alkyl group, an N-alkylacylamino group, an N-aralkylacylamino group or an N,N-dialkylamino group;

a benzoyl group which may be optionally substituted with a halogen atom, a nitro group or an alkyl group, an alkoxycarbonyl group, an N-alkylacylamino group, an N-aralkylacylamino group, an alkylthio group, an aralkylthio group, an arylthio group, a formyl group, an N,N-dialkylamino group, an optionally substituted alkenyl group, an optionally substituted alkynyl group, or a piperidyl group, n denotes an integer from 0 to 4, or Xn, together with the benzene ring to which it is bonded, may form a quinoline, fluorene, or naphthalene group, and $R^1$ denotes an alkyl group, an alkenyl group, an aryl group, an aralkyl group, an alkoxy group, an aryloxy group or an aralkyloxy group, which comprises reacting a nitroaniline compound of formula (2);

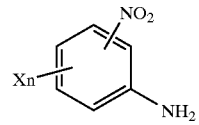

(2)

wherein X and n are the same as described above, with an acid anhydride of formula (3a) or an acid chloride of formula (3b):

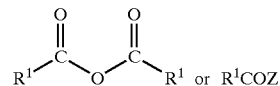

(3b)

wherein $R^1$ is the same as defined above and Z denotes a halogen atom, in the presence of an alkali metal compound or an alkaline earth metal compound in an amount of about 1.6 moles or more per mol of a nitroaniline compound of formula (1), and a method for producing an N-acylnitroaniline derivative of formula (4);

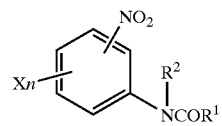

(4)

wherein $R^1$ is the same as defined above and $R^2$ denotes an optionally substituted alkyl group, an optionally substituted alkenyl group, or an optionally substituted alkynyl group, and X and n denote the same as described above, which comprises reacting the resulting product obtained in the above-described method with a compound of formula (5);

$R^2$—Y wherein $R^2$ denotes the same as defined above and Y denotes a leaving group.

DETAILED DESCRIPTION OF THE INVENTION

First, a description will be made to the production method of obtaining N-acylnitroaniline derivative of formula (1).

In the compounds disclosed in the present invention, the halogen atoms denoted by X or Z include fluorine, chlorine, bromine and iodine atoms.

The alkyl group in the haloalkyl group, the alkoxy group, the phenylalkyl group, the alkoxycarbonyl group, the phenylalkoxyl group, the N-alkylacylamino group, the N,N-dialkylamino group, and the alkylthio group include an alkyl group of 1 to 10 carbon atoms.

In the N-aralkylacylamino group and the aralkylthio group, the alkyl moiety include an alkyl groups of 1 to 6 carbon atoms such as a methyl group, an ethyl group, n-propyl group, i-propyl group, t-butyl group, n-butyl group, s-butyl group, n-pentyl group, i-pentyl group, n-hexyl group, or the like.

Examples of the aryl groups in the aralkyl, (C6–C10)aryl group, arylthio and the following aroyl groups include a phenyl group, a naphthyl group and the like. Examples of the arylthio group include a phenylthio group, a naphthylthio group and the like.

Examples of the acyl group of the N-alkylacylamino group and N-aralkylacylamino group include a (C1–C6) alkanoyl or (C6–C10)aroyl group, which may be substituted, for example, with a halogen atom. Specific examples of the acyl group include a formyl group, an acetyl group, a pivaloyl group, a trifluoroacetyl group, a trichloroacetyl group, a benzoyl group, a 2-chlorobenzoyl group, 1- or 2-naphthoyl group and the like. Other examples of acyl groups of N-aralkylacylaminxo group will be apparent to one skilled in the art.

Examples of the optionally substituted alkenyl group include chain, branched or cyclic alkenyl groups of 2 to 10 carbon atoms, which may be substituted with a halogen atom, an alkoxyl group of 1 to 6 carbon atoms, or a halogenoaryl group of 6 to 10 carbon atoms. The halogenoaryl group of 6 to 10 carbon atoms include a phenyl or naphthyl group which is substituted with at least one halogen atom. Specific examples of the halogenoaryl group include a chlorophenyl, dichlorophenyl, bromophenyl, fluorophenyl, difluorophenyl, or iodophenyl group and the like.

Specific examples of the optionally substituted alkenyl group include a vinyl group, a 2,2-dimethylvinyl group, a 1-propenyl group, a 1-butenyl group, a cyclohexenyl group and the like.

Examples of the optionally substituted alkynyl group include an alkynyl group of 2 to 10 carbon atoms, which may be substituted with a halogen atom, an alkoxy group of 1 to 6 carbon atoms, an aryl group of 6 to 10 carbon atoms, a halogenoaryl of 6 to 10 carbon atoms, a trialkyl(C1–C4) silyl group and the like.

Specific examples of the optionally substituted alkynyl group include a trimethylsilylethynyl group, a 1-propynyl group, a 1-butynyl group and the like. The nitroaniline compounds of formula (2) are commercially available or can be produced by known methods.

Specific examples of the nitroaniline compound (2) include 2-nitroaniline, 2-bromo-4,6-dinitroaniline, 6-chloro-2,4-dinitroaniline, 2,4-dinitroaniline, 2,6-dinitroaniline, 2,4-dinitro-5-fluoroaniline, 4-methoxy-2-nitroaniline, 4-ethoxy-2-nitroaniline, 4-amino-3-nitrobenzophenone, 4-amino-3-nitrobenzofluoride 2,6-dinitro-4-methylaniline, 2,4-dichloro-6-nitroaniline, 4,6-dimethyl-2-nitroaniline, 2-methyl-6-nitroaniline, 4,5-dichloro-2-nitroaniline, 5-chloro-2-nitroaniline, 4,5-dimethyl-2-nitroaniline, 5-methyl-2-nitroaniline, 4-fluoro-2-nitroaniline, 4-chloro-2-nitroaniline, 4-methyl-2-nitroaniline, 4,5-difluoro-2-nitroaniline, 2,4-dibromo-6-nitroaniline, 4-amino-3-nitrobenzonitrile, methyl 4-amino-3-nitrobenzoate, 2-amino-3-nitro-9-fluorenone, 4-benzyloxy-2-nitroaniline, 3,3'-dinitrobenzidine, 2,4-dimethyl-3,6-dinitroaniline, 2,4-dinitro-6-phenylaniline, 4-methoxy-3-methyl-6-nitroaniline, 3-bromo-4-methoxy-6-nitroaniline, 3-amino-2-nitrofluorene, 5-ethoxy-4-fluoro-2-nitroaniline, 2,4-difluoro-6-nitroaniline, 5-chloro-4-methyl-2-nitroaniline, 4-ethyl-2-nitroaniline, 4-nitroaniline, 2-bromo-4,6-dinitroaniline, 6-chloro-2,4-dinitroaniline, 2,5-dimethoxy-4-nitroaniline, 2-cyano-4-nitroaniline, 2-methoxy-4-nitroaniline, 2-amino-5-nitrobenzophenone, 2-amino-5-nitrobenzotrifluoride, 2,6-dibromo-4-nitroaniline, 2-chloro-4-nitroaniline, 2,6-dichloro-4-nitroaniline, 2methyl-4-nitroaniline, 5-methoxy-2-methyl-4-nitroaniline, 5-amino-2-nitrobenzotrifluoride, 2-bromo-6-chloro-4-nitroaniline, 2-ethoxy-4-nitroaniline, 2-bromo-4-nitroaniline, 2,5-dichloro-4-nitroaniline, 2,5-dimethyl-4-nitroaniline, 5-nitro-2-biphenylamine, 5-methyl-4-nitro-o-anisidine, 3-chloro-6-methyl-4-nitroaniline, 2-amino-3,5-dinitrobenzonitrile, 6-bromo-2-cyano-4-nitroaniline, 3-chloro-4-nitroaniline, 3-methyl-4-nitroaniline, 4,5-dinitro-2-methylaniline, 5-chloro-2-methoxy-4-nitroaniline, 6-chloro-2-cyano-4-nitroaniline, 3,5-dimethyl-4-nitroaniline, 2-chloro-4-nitro-5-piperidine-4-yl-phenylamine, 2,6-dimethyl-4-nitroaniline, ethyl 2-amino-4-chloro-5-nitrobenzoate, 2-(benzyloxy)-4-nitroaniline, methyl 2-amino-5-nitrobenzoate, 4,6-dinitro-o-toluidine, 3,5-dichloro-4-nitroaniline, 2-sec-butyl-4,6-dinitro-phenylamine, 2-amino-5-nitro-2'-chlorobenzophenone, 2-chloro-6-methyl-4-nitroaniline, 4-nitro-2,5-diethoxyaniline, N-methyl-(2-amino-3-nitro)-acetanilide, 2-amino-5-nitro-4-(p-tolylthio)-anisole, 5-amino-6-nitroquinoline, 2-amino-1-nitronaphthalene, 2-nitro-1-naphthylamine, 1-amino-4-nitronaphthalene, 2-bromo-4-nitro-1-naphthylamine and the like.

The alkali metal compound or the alkaline earth metal compound is preferably alkali metal hydride (e.g., sodium hydride, lithium hydride, potassium hydride or the like) or alkaline earth metal hydrides (e.g., calcium hydride, or the like) and among them, sodium hydride is preferred.

The amount of the alkali metal compound or the alkaline earth metal compound to be used is usually about 1.6 moles or more, preferably 1.8 mole or more, and may be up to 5 moles, per mol of the nitroaniline compound (2) with amount greater than 5 moles being within the scope of the invention.

Examples of the acid anhydride include an aliphatic acid anhydride having 2 to 10 carbon atoms such as acetic anhydride, propionic anhydride, isovalereic anhydride, pivalic anhydride, or the like, an unsaturated aliphatic acid anhydride having 3 to 10 carbon atoms such as acrylic acid anhydride or the like, an aromatic carboxylic acid anhydride, of which the aromatic ring (e.g., phenyl, naphthyl or the like) may be substituted with a halogen atom, a nitro group, an alkyl group having C1 to C4 carbon atoms (e.g., methyl, ethyl, n-propyl, i-propyl, n-butyl, t-butyl, s-butyl or the like) or an alkoxy group having C1 to C4 carbon atoms (e.g., methoxyl, ethoxy, n-propoxy, i-propoxy, n-butoxy, t-butoxy, s-butoxy or the like), and a dialkyl dicarbonate including a (C1–C4)dialkyl dicarbonate such as dimethyl bicarbonate, diethyl dicarbonate, di-t-butyl dicarbonate or the like.

Examples of the acyl halide (e.g., fluoride, chloride, bromide or iodide) include:

an aliphatic acid halide having 2 to 10 carbon atoms such as acetyl chloride, propionyl chloride, butyryl chloride, isobutyryl chloride, valeryl chloride, isovareryl chloride, pivaloyl chloride, hexanoyl chloride, heptanoyl chloride, octanoyl chloride, nonanoyl chloride, decanoyl chloride or the like, an unsaturated aliphatic acid halide having 3 to 10 carbon atoms such as acryloyl chloride, propioloyl chloride, methacryloyl chloride, crotonoyl chloride, isocrotonoyl chloride, 2-pentenoyl chloride, 2-hexenoyl chloride, 2-octenoyl chloride, 2-decenoyl chloride or the like an aromatic carboxylic acid halide, of which the aromatic ring (e.g., phenyl or naphthyl or the like) may be substituted with a halogen atom, a nitro group, C1 to C4 alkyl group, C1 to C4 alkoxy group such as benzoyl chloride, o-methylbenzoyl chloride, p-t-butylbenzoyl chloride, o-chlorobenzoyl chloride, m-chlorobenzoyl chloride, p-chlorobenzoyl chloride, p-nitrobenzoyl chloride, naphthoyl chloride, or the like, a (C1–C4)alkyl chlorocarbonate such as methyl chlorocarbonate, ethyl chlorocarbonate, propyl chlorocarbonate, isopropyl chlorocarbonate, isobutyl chlorocarbonate, and an aralkyl chlorocarbonate such as benzyl chlorocarbonate or the like. Specific examples of the acyl halide include fluoride, bromides and iodides, which correspond to the chlorides as specified above. Among the halides, preferred is the chloride and bromide, more preferred is the chloride.

The amount of the acyl anhydride (3a) or acyl halide (3b) used in the present invention is preferably from about 0.8 to about 1.5 moles, more preferably about 0.9 to about 1.3 moles per mol of the nitroaniline compound (2).

A solvent is preferably used in this reaction, and examples of the solvent that may be used include:

ether solvents such as tetrahydrofuran, diethyl ether, t-butyl methyl ether, dimethoxyethane, dioxane, or the like, polar solvents such as dimethylformamide, dimethylacetamide, dimethylsulfoxide or the like, aromatic hydrocarbon solvents such as toluene, xylene, benzene or the like, halogenated hydrocarbon solvents such as chlorobenzenes, and hydrocarbon solvents such as hexane, heptane and the like.

Preferred are ether solvents such as tetrahydrofuran, diethyl ether, t-butyl methyl ether, dimethoxyethane, dioxane and the like and aprotic polar solvents such as dimethylformamide, dimethylacetamide, dimethylsulfoxide or the like. These solvents may be used alone or in a mixture of two or more of them.

The concentration of the N-acylnitroaniline derivative of formula (1) in the solvent is not particularly limited, however the reaction is preferably carried out by controlling the concentration of the N-acylnitroaniline derivative in the solvent so that it is within a range from about 0.1 to about 50% by weight, and preferably is within a range from about 1 to about 20% by weight.

Any suitable reaction temperature may be used in the present invention. Preferably, the reaction temperature is set within a range from a temperature higher than the solidification point of the system to a reflux temperature, and more preferably is within a range from about –10° C. to the reflux temperature, After completion of the reaction, the desired product can be obtained by any suitable conventional technique including adding the reaction solution to water and subjecting the solution to an extraction or concentration method, and purification of the product may be carried out by column chromatography, crystallization, or any other suitable method, if necessary. The reaction solution may be used as it is in a subsequent process to produce a pharmaceutical or an agricultural product.

In the production method of the present invention as described above, the N-acylnitroaniline derivative of formula (2) may be isolated and used for a subsequent reaction step, however, it is preferred from an industrial production process standpoint to react the same, without being isolated, with the compound of formula (5) for producing the N-acylnitroaniline derivative of formula (4).

Next, the production method for producing an N-acylnitroaniline derivative of formula (4) will be described.

With regard to $R^2$ of the compound of formula (5), the optionally substituted alkyl group includes, for example, an alkyl group of 1 to 10 carbon atoms which may be substituted with at least one group selected from a halogen atom, an alkoxy of 1 to 6 carbon atoms, an (C1–C4)alkoxy- or (C7–C11)aralkyloxy-carbonyl group, an aryl of 6 to 10 carbon atoms, a (C6–C10) halogenoaryl group and the like. The (C6–C10) halogenoaryl group means the same groups as specified for $R^1$ above.

The optionally substituted alkenyl group includes, for example, an alkenyl group of 2 to 10 carbon atoms which may be substituted with a group selected from a halogen atom, an alkoxy of 1 to 6 carbon atoms, an aryl of 6 to 10 carbon atoms, a halogenoaryl of 6 to 10 carbon atoms and the like.

The optionally substituted alkynyl group includes, for example, an alkynyl group of 2 to 10 carbon atoms which may be substituted with a group selected from a halogen atom, an alkoxy of 1 to 6 carbon atoms, an aryl of 6 to 10 carbon atoms, a halogenoaryl of 6 to 10 carbon atoms and the like.

The leaving group "Y" in the compound of formula (5) include a halogen atom, or an $OS(O)_2R^2$ group, wherein $R^2$ represents an alkoxyl group (e.g., an alkoxy group of 1 to 10 carbon atoms such as methoxy, ethoxy, n-propoxy, n-butoxy, n-pentyloxy, hexyloxy, heptyloxy, octyloxy, nonyloxy, decyloxy or the like), an alkyl group optionally substituted with a halogen atom (e.g., methyl, ethyl, propyl, trifluoromethyl, chloromethyl, chloroethyl, n-propyl, n-butyl, n-penty, hexyl, heptyl, octyl, nonyl, decyl or the like), or an aryl group optionally substituted with an alkyl group(e.g., C1–C4 alkyl such as methyl, ethyl, propyl, butyl or the like) or a halogen atom (e.g., phenyl, naphthyl, tolyl, chlorophenyl, bromophenyl or the like).

Examples of the halogen atom include chlorine, bromine and iodine.

Specific examples of the compounds of formula (5) suitable for the present invention include, for example, a haloalkyl group such as methyl chloride, propyl chloride, butyl chloride, methyl bromide, ethyl bromide, propyl bromide, butyl bromide, isobutyl bromide, isopropyl bromide, pentyl bromide, methyl iodide, ethyl iodide, pentyl iodide, isobutyl iodide, isopropyl iodide, isopentyl iodide, cyclohexyl iodide, butyl iodide, propyl iodide, heptyl iodide, and the like an aralkyl halide such as benzyl bromide, benzyl chloride, or the like, ethyl bromoacetate, methyl bromoacetate, tert-butyl bromoacetate, benzyl bromoacetate, ethyl iodoacetate, an alkenyl halide such as allyl chloride, allyl iodide or the like, a sulfonic acid ester such as alkyl methanesulfonate, alkyl chloromethanesulfonate, alkyl p-toluenesulfonate, alkyl trifluoromethanesulfonate, alkyl nonafluorobutanesulfonate, a dialkyl sulfate, wherein the alkyl denotes a methyl group, an ethyl group, a propyl group, a butyl group, an isopropyl group, an isobutyl group, or an alkenyl or aralkyl sulfate such as a diallyl sulfonate, a dibenzyl sulfonate, and the like.

Any suitable amount of the compound of formula (5) may be used in the reaction, and the amount is preferably about 0.8 to about 3 moles, more preferably about 0.9 to about 2 moles, per mol the compound of formula (1).

A solvent is preferably used for this reaction, and examples of the solvent include, for example, ether solvents such as tetrahydrofuran, diethyl ether, t-butyl methyl ether, dimethoxyethane, dioxane, and the like, aprotic polar solvents such as dimethylformamide, dimethylacetamide, dimethylsulfoxide and the like, aromatic hydrocarbon solvents such as toluene, xylene, benzene and the like, halogenated hydrocarbon solvents such as chlorobenzene, and hydrocarbon type solvents such as hexane, heptane and the like.

Preferred are ether solvents such as tetrahydrofuran, diethyl ether, tert-butyl methyl ether, dimethoxyethane, dioxane and the like and polar solvents such as dimethylformamide, dimethylacetamide, dimethylsulfoxide and the like. These solvents may be used alone or in a mixture of two or more of them.

Any suitable reaction temperature may be used in the present invention. Preferably, the reaction temperature is set within a range from a temperature higher than the solidification point of the system to a reflux temperature, and more preferably is within a range from about −10° C. to the reflux temperature.

After completion of the reaction, the desired product can be obtained by any suitable conventional technique including extraction and concentration, which are conventional post-treatment processes, and if necessary, purification of the product may be carried out by column chromatography, crystallization, or other method.

According to the present invention, an N-acylnitroaniline derivative can be produced in the industrially advantageous manner.

EXAMPLES

Hereinafter, although the present invention will be more particularly described with reference to examples, it is not intended that the present invention is restricted by these examples.

Example 1

Production of N-t-butoxycarbonyl-2-nitroaniline 1.30 g of sodium hydride (60% content, 2.2 moles per mol of the nitroaniline compound) was suspended in 20.24 g of tetrahydrofuran and cooled with ice. To the obtained suspension, 22.20 g of a tetrahydrofuran solution containing 2.00 g of 2-nitroaniline was added, stirred for 10 minutes, allowed to stand at room temperature and stirred for 30 minutes. To the obtained mixture, 6.92 g of a tetrahydrofuran solution containing 3.41 g of di-t-butyl dicarbonate was added at room temperature and stirred for 2 hours. The reaction mixture was added to ice water and extracted with toluene to separate an organic layer and then the organic layer was analyzed by high performance liquid chromatography and the yield of the desired product was found to be 96%.

$^1$H-NMR (300 MHz, CDCl$_3$): d 9.66 (1H, brs), 8.57 (1H, d), 8.54 (1H, d), 7.61 (1H, dt), 7.08 (1H, dt), 1.55 (9H, s). $^{13}$C-NMR (75 MHz, CDCl$_3$): d 152.58, 136.33, 136.12, 126.20, 122.20, 121.06, 82.20, 28.58.

Example 2

Production of N-t-butoxycarbonyl-2-nitroaniline

The reaction was carried out in a similar manner as that of the example 1 except that the amount of sodium hydride (60% content) was changed to 1.03 g (1.8 moles per mol of the nitroaniline compound). Consequently, the yield of the desired product was 75%.

Example 3

Production of N-t-butoxycarbonyl-2-nitroaniline 1.30 g of sodium hydride (60% content) was suspended in 20.03 g of tetrahydrofuran and cooled with ice. To the obtained suspension, 22.51 g of a tetrahydrofuran solution containing 2.00 g of 4-nitroaniline was added, stirred for 10 minutes, allowed to stand at room temperature and stirred for 30 minutes. To the obtained mixture, 3.44 g of di-t-butyl dicarbonate was added at room temperature and stirred for 2 hours. The reaction mixture was added to ice water and extracted with toluene to separate an organic layer and then the organic layer was analyzed by high performance liquid chromatography to find the yield of the desired product was 97%.

$^1$H-NMR (300 MHz, CDCl$_3$): d 8.20–8.13 (2H, m), 7.57–7.50 (2H, m), 7.00 (1H, brs), 1.53 (9H, s). $^{13}$C-NMR (75 MHz, CDCl$_3$): d 151.92, 144.57, 142.62, 125.19, 117.51, 81.95, 28.20.

Example 4

Production of N-t-butoxycarbonyl-chloro-2-nitroaniline 1.10 g of sodium hydride (60% content) was suspended in 20.43 g of tetrahydrofuran and cooled with ice. To the obtained suspension, 22.74 g of a tetrahydrofuran solution containing 1.99 g of 5-chloro-2-nitroaniline was added, stirred for 10 minutes, allowed to stand at room temperature and stirred for 30 minutes. To the obtained mixture, 5.51 g of a tetrahydrofurane solution containing 2.75 g of di-t-butyl dicarbonate was added at a room temperature and stirred for 2 hours. The reaction mixture was added to ice water and extracted with toluene to separate an organic layer and then the organic layer was analyzed by high performance liquid chromatography to find the yield of the desired product was 99%.

$^1$H-NMR (300 MHz, CDCl$_3$): d 9.77 (1H, brs), 8.70–8.68 (1H, m), 8.16–8.13 (1H, m), 7.08–7.02 (1H, m), 1.64 (9H, s).; $^{13}$C-NMR (75 MHz, CDCl$_{13}$): d 152.23, 143.03, 137.33, 134.37, 127.46, 122.47, 120.56, 82.80, 28.53.

Example 5

Production of N-t-butoxycarbonyl-4-cyano2-nitroaniline 1.06 g of sodium hydride (60% content) was suspended in 19.92 g of tetrahydrofuran and cooled with ice. To the obtained suspension, 20.75 g of a tetrahydrofuran solution containing 2.00 g of 4-cyano-2-nitroaniline was added, stirred for 10 minutes, allowed to stand at room temperature and stirred for 1 hr. To the obtained mixture, 4.79 g of a tetrahydrofuran solution containing 2.89 g of di-t-butyl dicarbonate was added at a room temperature and stirred for 2 hours. The reaction mixture was added to ice water and extracted with toluene to separate an organic layer and then the organic layer was analyzed by high performance liquid chromatography to find the yield of the desired product was 99%.

$^1$H-NMR (300 MHz, CDCl$_3$): d 9.90 (1H, brs), 8.81 (1H, d), 8.53 (1H, d), 7.82 (1H, dd), 1.56 (9H, s). $^{13}$C-NMR (75 MHz, CDCl$_3$): d 151.78, 140.01, 138.39, 135.31, 130.79, 121.62, 117.18, 105.64, 83.61, 28.45.

Example 6

Production of N-t-butoxycarbonyl-4-nitro-1-naphthylamine 0.92 g of sodium hydride (60% content) was suspended in 19.44 g of tetrahydrofuran and cooled with ice. To the obtained suspension, 20.78 g of a tetrahydrofuran solution containing 2.00 g of 4-nitro-1-naphthylamine was added, stirred for 10 minutes, allowed to stand at room temperature and stirred for 1 hour. To the obtained mixture, 5.09 g of a tetrahydrofuran solution containing 2.52 g of di-t-butyl dicarbonate was added at a room temperature and stirred for 4 hours. The reaction mixture was added to ice water and extracted with toluene to separate an organic layer and then the organic layer was analyzed by high performance liquid chromatography to find the yield of the desired product was 80%.

Example 7

Production of N-t-butoxycarbonyl-4-methoxycarbonyl-2-nitroaniline 0.57 g of sodium hydride (60% content) was suspended in 9.87 g of tetrahydrofuran and cooled with ice. To the obtained suspension, 9.86 g of a tetrahydrofuran solution containing 0.95 g of 4-methoxycarbonyl-2-nitroaniline was added, stirred for 10 minutes, allowed to stand at room temperature and stirred for 1 hour. To the obtained mixture, 2.67 g of a tetrahydrofuran solution containing 1.30 g of di-t-butyl dicarbonate was added at a room temperature and stirred for 3 hours. The reaction mixture was added to an ice-cooled aqueous saturated ammonium chloride solution and extracted with toluene to separate an organic layer and then the organic layer was analyzed by high performance liquid chromatography to find the yield of the desired product was 80%.

Example 8

Production of N-t-butoxycarbonyl-5-methoxy-2-nitroaniline 0.72 g of sodium hydride (60% content) was suspended in 7.05 g of tetrahydrofuran and cooled with ice. To the obtained suspension, 8.21 g of a tetrahydrofuran solution containing 1.00 g of 5-methoxy-2-nitroaniline was added, stirred for 10 minutes, allowed to stand at room temperature and stirred for 1 hour. To the obtained mixture, 1.46 g of di-t-butyl dicarbonate was added at room temperature and stirred for 2 hours. The reaction mixture was added to ice water and extracted with toluene to separate an organic layer and then the organic layer was analyzed by high performance liquid chromatography to find the yield of the desired product was 92%.

Example 9

Production of N-t-butoxycarbonyl-N-methyl-5-chloro-2-nitroaniline 1.01 g of sodium hydride (60% content) was suspended in 18.73 g of tetrahydrofuran and cooled with ice. To the obtained suspension, 22.76 g of a tetrahydrofuran solution containing 2.00 g of 5-chloro-2-nitroaniline was added, stirred for 10 minutes, allowed to stand at room temperature and stirred for 30 minutes. To the obtained mixture, 5.75 g of a tetrahydrofuran solution containing 2.77 g of di-t-butyl dicarbonate was added at room temperature and stirred for 2 hours. To the reaction mixture, 3.74 g of a tetrahydrofuran solution containing 1.86 g of methyl iodine was added at room temperature, heated to 60° C., and stirred for 10 hours. The reaction mixture was added to ice water and extracted with toluene to separate an organic layer and then the organic layer was analyzed by high performance liquid chromatography to find the yield of the desired product was 86%.

$^1$H-NMR (300 MHz, CDCl$_3$): d 7.91–7.87 (1H, m), 7.36–7.32 (2H, m), 3.30 (3H, s), 1.31 (9H, s). $^{13}$C-NMR (75 MHz, CDCl$_3$): d 144.74, 139.40, 138.72, 128.94, 127.11, 126.06, 82.09, 37.32, 27.74.

Example 10

Production of N-t-butoxycarbonyl-N-methyl-2-nitroaniline 1.25 g of sodium hydride (60% content) was suspended in 16.02 g of tetrahydrofuran and cooled with ice. To the obtained suspension, 22.68 g of a tetrahydrofuran solution containing 1.99 g of 2-nitroaniline was added, stirred for 10 minutes, allowed to stand at room temperature and stirred for 30 minutes. To the obtained mixture, 6.89 g of a tetrahydrofuran solution containing 3.44 g of di-t-butyl dicarbonate was added at room temperature and stirred for 2 hours. To the reaction mixture, 18.04 g of toluene and 2.03 g of dimethyl sulfate were added at room temperature and stirred for 2 hours. The reaction mixture was added to ice water and extracted with toluene to separate an organic layer and then the organic layer was analyzed by high performance liquid chromatography to find the yield of the desired product was 92%.

Example 11

Production of N-t-butoxycarbonyl-N-methyl-5-methoxy-2-nitroaniline 13.10 g of sodium hydride (60% content) was suspended in 175.31 g of tetrahydrofuran and cooled with ice. To the obtained suspension, 227.53 g of a tetrahydrofuran solution containing 25.03 g of 5-methoxy-2-nitroaniline was added, stirred for 10 minutes, allowed to stand at room temperature and stirred for 30 minutes. To the obtained mixture, 35.73 g of di-t-butyl dicarbonate was added at room temperature and stirred for 3 hours. To the reaction mixture, 249.76 g of toluene and 28.74 g of dimethyl sulfate were added at room temperature and stirred for 2 hours. The reaction mixture was added to ice water and extracted with toluene to separate an organic layer and then the organic layer was analyzed by high performance liquid chromatography to find the yield of the desired product was 94%.

Comparative Example 1

Production of N-t-butoxycarbonyl-2-nitroaniline

The reaction was conducted in a similar manner as that of the example 1 except that the amount of sodium hydride (60% content) was changed to 0.85 g (1.5 moles per mol of the nitroaniline compound). Consequently, the yield of the desired product was 48%.

Example 12

Production of N-acetyl-2-nitroaniline 1.89 g of sodium hydride (60% content) was suspended in 23.76 g of tetrahydrofuran and cooled with ice. To the obtained suspension, 23.79 g of a tetrahydrofuran solution containing 3.00 g of 2nitroaniline was dropwise added over 1 hour, stirred for 10 minutes, allowed to stand at room temperature and stirred for 30 minutes. To the obtained mixture, 2.41 g of acetic anhydride was added dropwise over 1 hr at room temperature and stirred for 2 hours. Then, water was added to the reaction mixture, and extraction and separation were conducted. The obtained organic layer was analyzed by high performance liquid chromatography to find the yield of the desired product was 84%.

$^1$H-NMR (300 MHz, CDCl$_3$): 10.33 (1H, brs), 8.76 (1H, dd), 8.21 (1H, dd), 7.65 (1H, dt), 7.18 (1H, dt), 2.30 (3H, s).; $^{13}$C-NMR (75 MHz, CDCl$_3$): 169.06, 136.34, 135.98, 134.87, 125.73, 123.23, 122.19, 25.63.

Example 13

Production of N-benzoyl-2-nitroaniline 1.58 g of sodium hydride (60% content) was suspended in 19.80 g of tetrahydrofuran and cooled with ice. To the obtained suspension, 19.83 g of a tetrahydrofuran solution containing 2.50 g of 2-nitroaniline was dropwise added over 1 hour, stirred for 10 minutes, allowed to stand at room temperature and stirred for 30 minutes. To the obtained mixture, 2.77 g of benzoyl chloride was added dropwise over 0.5 hr at room temperature and stirred for 2 hours. The reaction mixture was added to water and separated. The separated organic layer was washed with sodium hydroxide solution and saline to obtain an organic layer, which was analyzed by high performance liquid chromatography to find the yield of the desired product was 82%.

$^1$H-NMR (300 MHz, CDCl$_3$): 11.36 (1H, brs), 9.01 (1H, dd), 8.28 (1H, dd), 8.10–7.96 (2H, m), 7.80–7.67 (1H, m), 7.67–7.50 (3H, m), 7.31–7.15 (1H, m). $^{13}$C-NNR (75 MHz, CDCl$_3$): 166.11, 136.83, 136.59, 135.74, 134.41, 133.03, 129.43, 127.75, 126.30, 123.69, 122.49.

Example 14

Production of N-benzyloxycarbonyl-2-nitroaniline 1.89 g of sodium hydride (60% content) was suspended in 23.76 g of tetrahydrofuran and cooled with ice. To the obtained suspension, 23.1 g of a tetrahydrofuran solution containing 3.00 g of 2-nitroaniline was dropwise added over 1 hr, stirred for 10 minutes, allowed to stand at room temperature and stirred for 30 minutes. To the obtained mixture, 11.12 g of a 33% toluene solution containing benzyloxycarbonyl chloride was added dropwise over 1 hr at room temperature and stirred for 2 hours. To the reaction mixture, water was added at room temperature and extracted, and separated. The obtained organic layer was washed with water and analyzed by high performance liquid chromatography to find the yield of the desired product was 90%.

$^1$H-NMR (300 MHz, CDCl$_3$): 9.91(1H, brs), 8.57 (1H, dd), 8.18 (1H, dd), 7.66–7.59 (1H, m), 7.48–7.30 (5H, mn), 5.24 (3H, s).; $^{13}$C-NMR (75 MHz, CDCl$_3$): 152.96, 136.10, 135.89, 135.49, 135.31, 128.67, 128.56, 128.43, 125.88, 120.73, 67.62.

Example 15

Production of N-methyl-N-acetyl-2-nitroaniline 1.58 g of sodium hydride (60% content) was suspended in 19.8 g of tetrahydrofuran and cooled with ice. To the obtained suspension, 19.8 g of a tetrahydrofuran solution containing 2.50 g of 2-nitroaniline was added dropwise over 1 hr, stirred for 10 minutes, allowed to stand at room temperature and stirred for 30 minutes. To the obtained mixture, 2.01 g of acetic acid anhydride was added over 1 hr at room temperature and stirred for 2 hours. To the reaction mixture, 2.49 g of dimethyl sulfate were added at room temperature and stirred for 1 hr. The reaction mixture was added to water and the separated organic layer was washed with saline then the organic layer was analyzed by high performance liquid chromatography to find the yield of the desired product was 78%.

$^1$-NMR (300 MHz, CDCl$_3$): 8.00 (1H, dd), 7.70 (1H, dd), 7.65 (1H, dt), 7.62–7.53 (1H, m), 7.50–7.37 (1H, m), 3.22 (3H, s), 1.83(3H, s).

Comparative Example 2

Production of N-acetyl-2-nitroaniline

An experiment was conducted in a similar manner as in Example 1 except the charged amount of sodium hydride (60% content) was changed to 0.95 g (1.1 moles per mol of the nitroaniline compound).

The invention being thus described, it will be apparent that the same may be varied in many ways. Such variations are to be regarded as within the spirit and scope of the invention, and all such modifications are intended to be included within the scope of the following claims.

What is claimed is:

1. A method for producing an N-acylnitroaniline derivative of the formula (1):

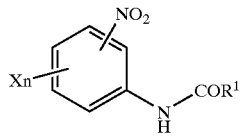

wherein X may be the same or different and denotes
- a hydrogen atom, a halogen atom, an alkyl group, a haloalkyl group, an alkoxy group, a phenylalkyl group, a phenylalkoxyl group,
- a phenyl group, a benzoyl group, an alkoycarbonyl group,
- an N-alkylaclyamino group, an aralkylacylamino group, an alkylthio group, an aralkylthio group, an arylthio group,
- a formyl group, an N,N-dialkylamino group,
- an alkenyl group,
- an alkynyl group, or a piperidyl group,
- n denotes an integer from 0 to 4,
- $R^1$ denotes an alkyl group, an alkenyl group, an aryl group, an aralkyl group, an alkoxy group, an aryloxy group or an aralkyloxy group, which comprises reacting a nitroaniline compound of formula (2):

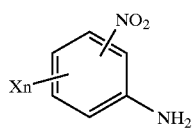

wherein X and n are the same as described above with an acid anhydride of formula (3a) or an acid halide of formula (3b):

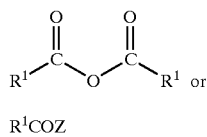

wherein $R^1$ is the same as defined above and Z denotes a halogen atom, in the presence of a hydride of an alkali or an alkaline earth metal, the hydride of an alkali or an alkaline earth metal being present in an amount of about 1.8 moles or more per mol of nitroaniline compound, wherein the nitro group in the formulas (1) and (2) is located at an opposition in relation to the amino group.

2. The method according to claim 1, wherein X is a phenyl group which may be substituted with a halogen, a nitro group, an alkyl group, an N-alkylacylamino group, an N-aralkylacylamino group or an N,N-dialkylamino group.

3. The method according to claim 1, wherein X is a benzoyl group which may be substituted with a halogen, a nitro group or an alkyl group.

4. A method for producing an N-acylnitroaniline derivative of formula (1):

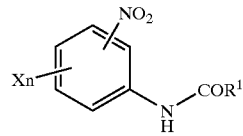

wherein Xn, together with the benzene ring to which it is bonded, forms a quinoline, fluorene, or naphthyl group, and $R^1$ denotes an alkyl group, an alkenyl group, an aryl group, an aralkyl group, an alkoxy group, an aryloxy group or an aralkyloxy group, which comprises reacting a nitroaniline

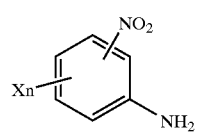

compound of formula (2):
wherein Xn is the same as described above, with an acid anhydride of formula (3a) or an acid halide of the formula (3b):

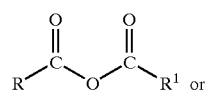

$R^1COZ$ (3b)

wherein $R^1$ is the same as defined above and Z denotes a halogen atom, in the presence of an alkali metal compound or an alkaline earth metal compound, the alkali metal compound or an alkaline earth metal compound being present in an amount of about 1.8 moles or more per mol of nitroaniline compound.

5. A method for producing an N-acylnitroaniline derivative of formula (4):

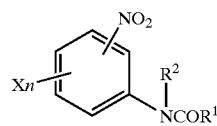

wherein $R^1$ denotes an alkyl group, an alkenyl group, or an alkynyl group,
- X may be the same or different and denotes a hydrogen atom, a halogen atom, an alkyl group, a haloalkyl group, an alkoxy group,
- a phenylalkyl group, a phenylalkoxyl group
- a phenyl group, a benzoyl group, an alkoxycarbonyl group,
- an N-alkylacylamino group, an N-aralkylacylamino group, an alkylthio group, an aralkylthio group, an arylthio group, a formyl group, an N,N-dialkylamino group, an alkenyl group, an alkynyl group, or a piperidyl group,
- n denotes an integer from 0 to 4,
- $R^2$ denotes an alkyl group, an alkenyl group, or an alkynyl group and Y denotes a leaving group, which comprises a reacting a nitroaniline compound of formula (2);

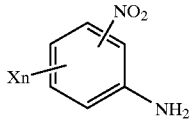
(2)

wherein X and n are the same as described above, with an acid anhydride of formula (3a) or an acid chloride of formula (3b):

(3a)

or

R$^1$COZ (3b)

wherein R$^1$ is the same as defined above and Z denotes a halogen atom, in the presence of a hydride of an alkali or alkaline earth metal, the hydride of an alkali or alkaline earth metal being present in an amount of about 1.8 moles or more per mol of the nitroaniline compound of formula (2), and then with a compound of formula (5);

R$^2$—Y (5)

wherein R$^2$ and Y are the same as described above, and wherein the nitro group in the formulas (4) and (2) is located at an opposition in the relation to the amino group.

6. The method according to claim 5, wherein X is a phenyl group which may be substituted with a halogen, a nitro group, an alklyl group, an N-alkylacylamino group, an N-aralkylacylamino group or an N,N-dialkylamino group.

7. The method according to claim 5, wherein X is a benzoyl group, which may be substituted with a halogen, a nitro group, an alkyl group, or an alkoxycarbonyl group.

8. A method for producing an N-acylnitroaniline derivative of formula (4):

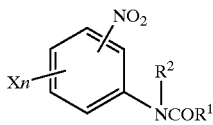
(4)

wherein R$^1$ denotes an alkyl group, an alkenyl group, an aryl group, or an alkynyl group, Xn, together with the benzene ring to which it is bonded, forms a quinoline, fluorene, or naphthalene group, and R$^2$denotes an alkyl group, an alkenyl group or an alkynyl group, and Y denotes a leaving group, which comprises reacting a nitroaniline compound of formula (2):

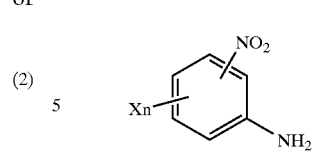
(2)

wherein Xn is the same as described above, with an acid anhydride of formula (3a) or an acid halide of formula (3b);

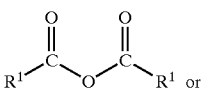
(3a)

R$^1$COZ (3b)

wherein R$^1$ is the same as defined above and Z denotes a halogen atom, in the presence of an alkali metal compound or an alkaline earth metal compound and then with a compound of formula (5):

R$^2$—Y (5)

wherein R$^2$ and Y are the same as described above.

9. The method according to claim 4, wherein the alkali or alkaline earth metal compound is a hydride of an alkali or an alkaline earth metal.

10. The method according to claim 8, wherein the alkali or alkaline earth metal compound is a hydride of an alkali or an alkaline earth metal.

11. The method according to claim 8, wherein the amount of the alkali or alkaline earth metal compound to be used is 1.8 moles or more per mol of the nitroaniline compound of formula (2).

12. The method according to claim 4, wherein the nitro group in the formulas (1) and (2) is located at an o- or p-position in relation to the amino group.

13. The method according to claim 8, wherein the nitro group in the formulas (1) and (2) is located at an o- or p-position in relation to the amino group.

14. The method according to claim 1, wherein the nitroaniline compound of formula (2) is 5-methoxy-2-nitroaniline.

15. The method according to claim 5, wherein the nitroaniline compound of formula (2) is 5-methoxy-2-nitroaniline.

16. The method according to claim 1, wherein R$^1$ denotes a t-butoxy group.

17. The method according to claim 4, wherein R$^1$ denotes a t-butoxy group.

18. The method according to claim 5, wherein R$^1$ denotes a methyl group.

19. The method according to claim 8, wherein R$^1$ denotes a phenyl group.

20. The method according to claim 5, wherein the leaving group is a halogen atom, or an OSO$_2$R$^2$ group.

21. The method according to claim 8, wherein the leaving group is a halogen atom, or an OSO$_2$R$^2$ group.

* * * * *